(12) United States Patent
Burge

(10) Patent No.: US 6,322,751 B1
(45) Date of Patent: Nov. 27, 2001

(54) OPTRODE FOR THE DETECTION OF VOLATILE CHEMICALS

(76) Inventor: Scott Russell Burge, 8869 S. Myrtle Ave., Tempe, AZ (US) 85284

( * ) Notice: Subject to any disclaimer, the term of this patent is extended or adjusted under 35 U.S.C. 154(b) by 0 days.

(21) Appl. No.: 09/241,573

(22) Filed: Feb. 1, 1999

Related U.S. Application Data

(60) Provisional application No. 60/073,387, filed on Feb. 2, 1998.

(51) Int. Cl.[7] ............................ G01N 15/06; G01N 21/29; G01N 21/00
(52) U.S. Cl. ............... 422/68.1; 422/82.05; 436/139; 436/164; 436/172
(58) Field of Search ................. 422/68.1, 82.05, 422/82.06, 82.07; 436/165, 172; 356/445

(56) References Cited

U.S. PATENT DOCUMENTS

| 4,544,231 | * | 10/1985 | Peterson | 350/96.15 |
| 4,666,672 | * | 5/1987 | Miller et al. | 422/68 |
| 4,786,171 | * | 11/1988 | LeFebre et al. | 356/326 |
| 4,892,383 | * | 1/1990 | Klainer et al. | 350/96.29 |
| 5,107,133 | * | 4/1992 | Klainer et al. | 250/573 |
| 5,116,759 | * | 5/1992 | Klainer et al. | 435/288 |

* cited by examiner

Primary Examiner—Jill Warden
Assistant Examiner—Dwayne K Handy

(57) ABSTRACT

An improved optrode or chemical sensing device has a design and materials for enhanced analytical characteristics for detecting volatile compounds in atmospheres. Cost of manufacture is decreased, the life of the optrode is increased, and improved sensitivity and reproducibility of the results are provided.

14 Claims, 2 Drawing Sheets

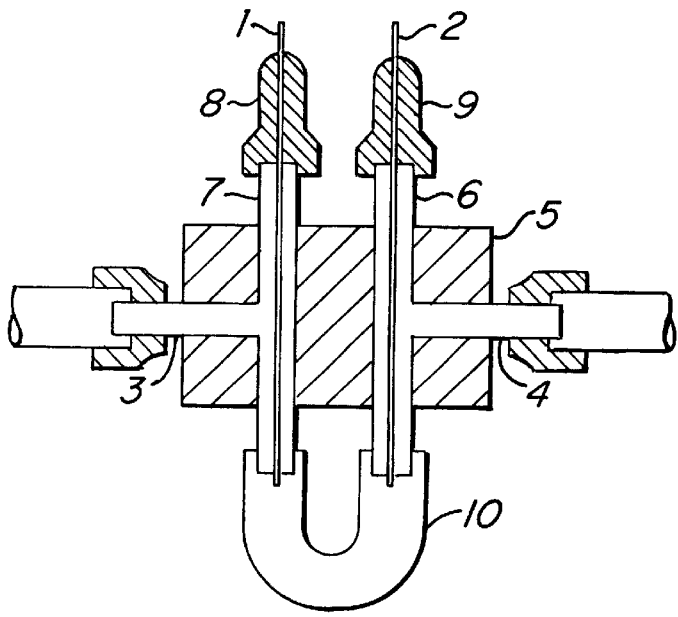
FIG.—1
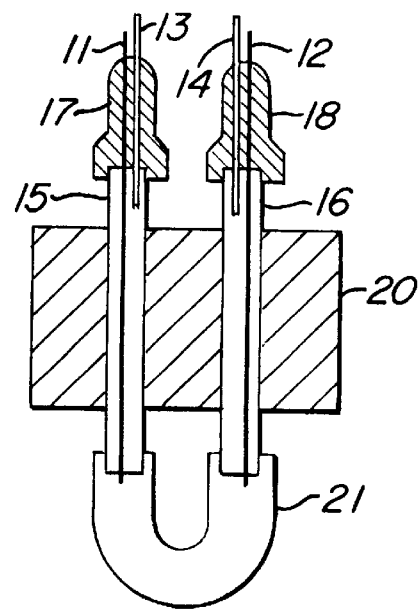
FIG.—2
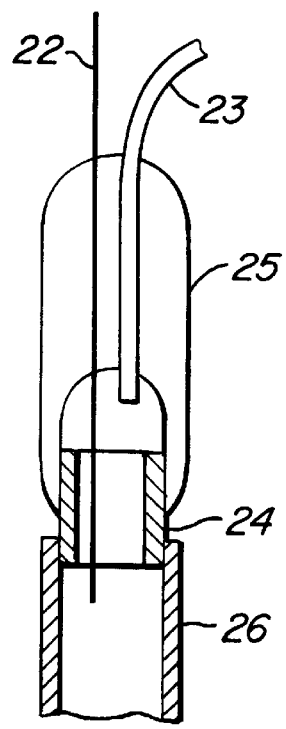
FIG.—3

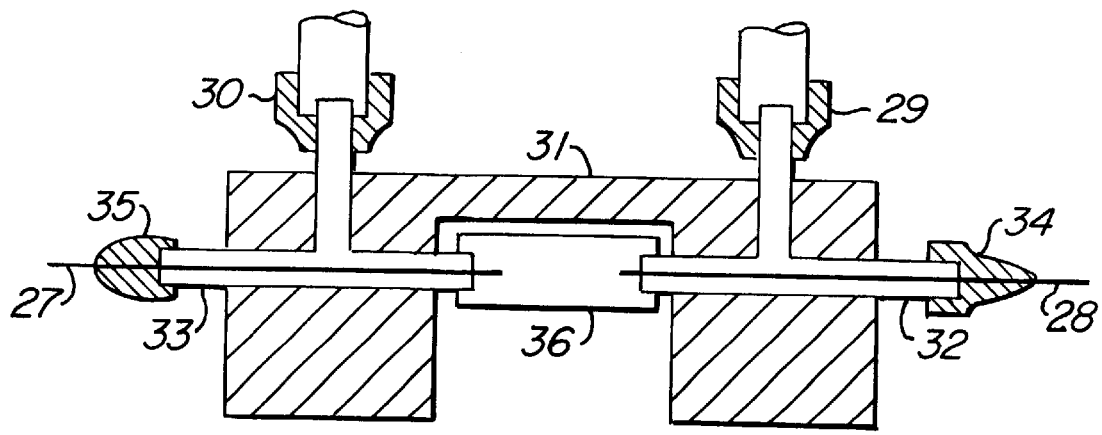
FIG.—4
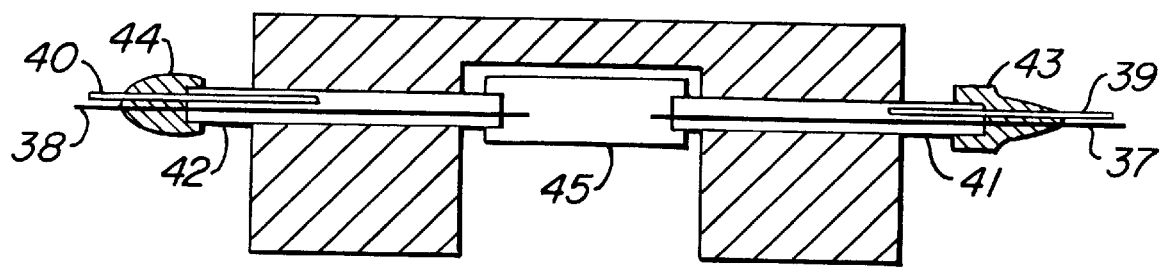
FIG.—5

OPTRODE FOR THE DETECTION OF VOLATILE CHEMICALS

RELATED APPLICATIONS

Reference is made to Applicant's U.S. Provisional Application Ser. No. 60/073,387, filed Feb. 02, 1998.

BACKGROUND OF THE INVENTION

This invention relates to a chemical sensor ("optrode") for the quantitative measurement of selected volatile organic and inorganic molecules in atmospheres. This is a refinement of the optrode design of Milanovich et al. The optrode has been modified in several important ways to allow for ease of manufacture and greater sensitivity.

The simplified design and operation of the optrode coupled with chemical specificity and low limits of detection makes the invention an attractive alternative to other forms of chemical analysis. The optrode has been shown to attain the precision and accuracy of gas chromatography with photoionization or Hall detectors for selected organic molecules, such as trichloroethene and chloroform. However, the optrode attains this performance without the need for preconcentration (such as purge and trap) or Hall detectors for selected organic molecules, such as thichloroethene and chloroform. However, the optrode attains this performance without the need for preconcentration (such as purge and trap) or separation (chromatography) steps. The optrode has been found to have a limit of detection of 1 part per billion of trichloroethene in water with 1,2-dichloroethene and tetrachloroethene present. Because of these performance factors and the ease of use of the optrode, there are many applications in environmental, health & safety, medical and process control fields for such a chemical sensor.

One of the important applications of the optrode is the creation of "real-time" sampling/analytical units for the monitoring of trichloroethene in ground water. The cost savings to the government and industry in avoiding the cost of manually sampling the sells, disposal of the purge water and the cost of the analytical laboratory over the lifetime of a ground-water restoration project can be significant.

Current optrode technology is divided into two primary types of designs. The most prevalent type of design in the literature is fabricating the optrode body from some type of inert material, and providing a port or area in the wall to be fitted with a permeable material. The species of interest, i.e. trichloroethene, passes through the permeable membrane and reacts with the reagent contained within the body of the sensor. Examples of the first type of optrode are Klainer et al., U.S. Pat. No. 5,116,759, and Miller et al., U.S. Pat. No. 4,666,674. The second type of optrode uses a permeable tube which serves as the body of the optrode. This type of sensor was developed by Milanovich it al. at Lawrence-Livermore National Laboratory, Livermore, Calif. The original design was disclosed in a series of papers. The design was very difficult to manufacture and suffered from several material compatibility problems. The reagents used in the design attacked the seals and other components reducing the life of the optrode.

This invention relates to a simplified design of the optrode which increases the life of the device while providing lower noise and resolution of other associated problems.

SUMMARY OF THE INVENTION

This invention is directed to the elimination of seals and dead space in the fabrication of the sensor first proposed by Milanovich et al. The seals were eliminated to reduce material compatibility problems and the dead space was eliminated to reduce probability of bubble formation. The reduction of the material compatibility problems increases the life of the optrode and significantly decreases the noise observed when analyzing very low concentrations of analytes. In particular it was found that various types of epoxy resins and stainless steel tubes were reacting with some reagents. Dead spaces were found to aid in the formation or entrapment of bubbles. When the air bubbles interfere with the light path, the optrode performance is degraded.

The best solution found for the elimination of the above factors while providing for ease of manufacture was to provide for the optic fiber to be centered inside and slightly projecting from the end of a small gauge fluorocarbon tube. The permeable fluorocarbon optrode body is then fitted over the outside diameter of the tube. The opposite side of the small gauge tube is either fitted into an inert block which allows for the independent introduction of the reagent from the side of the block, or the reagent enters the small gauge tube at the same point as the fiber optic. The sealing of the fiber optic with the fluorocarbon tube is accomplished with heat shrink fluorocarbon tubing.

BRIEF DESCRIPTION OF THE DRAWINGS

FIG. 1 illustrates a preferred embodiment of optrode according to the invention;

FIG. 2 illustrates an embodiment of the invention wherein fiber optics and reagent delivery tubes are introduced into the same optic tubes;

FIG. 3 illustrates a modified form of the optrode embodiment of FIG. 2, wherein the optrode is fabricated entirely of fluorocarbon components except for fiber optics; and FIGS. 4 and 5 illustrate embodiments of optrodes according to the invention wherein sensor bodies thereof are in alignment and the sensor bodies thereof are not curved as in the other embodiments.

DESCRIPTION OF THE PREFERRED EMBODIMENT

This optrode design is an improvement of the art which was first described by researchers at Lawrence-Livermore National laboratory (Milanovich et al.). The optrode has been modified in several important ways to allow for ease of manufacture and greater sensitivity. The inventions are described in five primary embodiments.

The first embodiment is illustrated in FIG. 1. The figure illustrates a design in which the fiber optics 1 and 2 and reagent delivery tubes 3 and 4 are not introduced through the same openings in the mounting block 5. In this embodiment the metal or polymer reagent delivery tube 3 and 4 conducting the unreacted and reacted reagents are positioned in a different axis to the metal or polymer tubing 6 and 7 conducting the fiber optics. The drawing illustrates the reagent tubes and fiber optic tubes at right angles, however other angles are envisioned in this design. The ability to separate the entry of the fiber optics from the reagent delivery and waste tubes allows for the use of many types of fittings (such as chromatography fittings) to prevent the leakage of the reagents from the sensor body. Alternatively, the fiber optics 1 and 2 can be sealed to fiber optic tubes 6 and 7 with the use of heat shrink Teflon or other polymer tubing 8 and 9 providing for a reagent tight seal. The fiber optics 1 and 2 may also be sealed in the fiber optic tubes 6 and 7 with various epoxy, polymer and metal seals.

The reagent delivery tubes 3 and 4 may be sealed to the metal or polymer tubes for conducting reagent to and from the assembly using methods similar methods used in sealing the fiber optics to the fiber optic tubes. The fiber optic tubes 6 and 7 extend below the mounting block 5. The fiber optics 1 and 2 are centered within the fiber optic tubes and extend slightly below the fiber optic tubes 6 and 7. The sensor body 10 is composed of a porous fluorocarbon tube which is fitted to the bottom of the fiber optic tubes 6 and 7. This causes the sensor body 10 to assume a curved profile. The sensor 10 can be sealed to the fiber optic tubes 6 and 7 using chromatography fittings, wire twists, heat shrink polymers or pressure fittings.

FIG. 2 illustrates an optrode apparatus where the fiber optics 11 and 12 and the reagent delivery tubes 13 and 14 are introduced into the same polymer or metal fiber optic tubes 15 and 16. The fiber optics 11 and 12 and the reagent delivery tubes 13 and 14 are sealed into the polymer or metal fiber optic tubes 15 and 16 using heat shrink fluorocarbon or polymer tubes 17 and 18. The fiber optics tubes 15 and 16 can be mounted in a mounting block 20. The fiber optics 11 and 12 extend below the bottom of the fiber optic tubes 15 and 16. The porous fluorocarbon sensor body 21 is fitted to the bottom of the fiber optic tubes 15 and 16. This causes the sensor body 21 to assume a curved profile. The sensor body 21 can be sealed to the fiber optic tubes 15 and 16 using chromatography fittings, wire twists, heat shrink polymers or pressure fitting.

FIG. 3 illustrates a variation of the embodiment presented in FIG. 2. The embodiment is fabricated entirely with fluorocarbon components with the exception of the fiber optics. Thee are two assemblies to fabricate a complete optrode. Both the assemblies are exactly identical except one assembly delivers the reagent and one assembly is used to drain the reagent from the sensor body. Therefore, only one of the assemblies is described. This allows the optrode to operate with very reactive reagents. The fiber optic 22 and fluorocarbon delivery tube 23 are placed inside of fiber optic tube 25. The fiber optic tube 25 is composed of a heat shrink fluorocarbon. The fiber optic tube 25 is subjected to heat until the end of the reagent delivery tube 23 is just exposed. The opposite end of the fiber optic tube 25 is heat shrunk over a fluorocarbon sensor body mounting tube 24 in which the fiber optic 22 is allowed to extend slightly beyond the end of the sensor body mounting tube 24. The permeable sensor body 26 is attached to the sensor body mounting tube 24.

FIGS. 4 and 5 illustrate the two embodiments of the optrode which allows for the sensor bodies 36 and 45 to be oriented straight, without any curvature as illustrated in the previous two embodiments (FIGS. 1 and 2). This increases the light throughput of the optrode which decreases the need for high amplification of the resulting signal.

FIG. 4 illustrates a design in which the fiber optics 27 and 28 and reagent delivery tubes 29 and 30 are not introduced through the same opening in the mounting block 31. In this embodiment the metal or polymer reagent delivery tube 29 and 30 conducting the unreacted and reacted reagents are positioned at 90° to the metal or polymer fiber optic tubes 32 or 33 conducting the fiber optics. The drawing illustrates the reagent tubes and fiber optic tubes at right angles, however other angles are included in this design. The ability to separate the entry of the fiber optics from the reagent delivery and waste tubes allows for the use of many types of fittings (such as chromatography fittings) to prevent the leakage of the reagents from the sensor body. Alternatively, the fiber optics 27 and 28 can be sealed to fiber optic tubes 32 and 33 and polymer tubes 34 and 35 with the use of heat shrink Teflon or other polymer tubing providing for a reagent tight seal. The fiber optics 27 and 28 may also be sealed in the fiber optic tubes 32 and 33 with various epoxy, polymer and metal seals.

The reagent delivery tubes 29 and 30 may be sealed to the metal or polymer tubes using methods similar to those used in sealing the fiber optics to the fiber optic tubes. The sensor body 36 can be sealed to the fiber optic tubes 32 and 33 using chromatography fittings, wire twists or heat shrink polymers.

FIG. 5 illustrates am optrode apparatus where the fiber optics 37 and 38 and the reagent delivery tubes 39 and 40 are introduced into the same polymer or metal fiber optic tubes 41 and 42. The fiber optics 37 and 38 and the reagent delivery tubes 39 and 40 are sealed into the polymer or metal fiber optic tubes 41 and 42 and polymer tubes 43 and 44 using heat shrink Teflon or polymer tubes. This modification allows for quick, reliable installation of the tubes. The sensor body 45 can be sealed to the fiber optic tubes 41 and 42 using chromatography fittings, wire twists or heat shrink polymers.

The inventor claims:

1. A chemical sensing device comprising:
   (a) a tube,
   (b) a reagent tube means of conducting reagent into and from said chemical sensing device,
   (c) a fiber optic means of conducting light into and from said chemical sensing device,
   (d) a permeable tube means of containing reagent during measurement,
   (e) a means for attachment of said reagent tube and said fiber optic along the same axis to one end of said tube, and
   (f) attachment of said permeable tube to the opposite end of said second tube.

2. The chemical sensing device of claim 1 wherein said first means for attaching said first reagent tube and said first fiber optic to the inlet end of said first fiber optic tube and said second means for attaching said second reagent tube and said second fiber optic to the inlet end of said second fiber optic tube are composed of heat shrink fluorocarbon polymer.

3. The chemical sensing device of claim 1 wherein said first reagent tube and said second regent tube are composed of fluorocarbon polymer.

4. The chemical sensing device of claim 1 wherein the permeable tube is formed into a loop.

5. The chemical sensing device of claim 1 wherein the permeable tube is formed without a loop.

6. The chemical sensing device of claim 1 wherein said first fiber optic tube and said second fiber optic tube are composed of fluorocarbon polymer.

7. The chemical sensing device of claim 1 wherein said first fiber optic tube and said second finer optic tube are composed of heat shrink fluorocarbon polymer.

8. A chemical sensing device comprising:
   (a) a tube,
   (b) a reagent tube means of conducting reagent into and from said chemical sensing device,
   (c) a fiber optic means of conducting light into and from said chemical sensing device,
   (d) a permeable tube means of containing reagent during measurement,
   (e) a seal means for attachment of said reagent tube to one end of said tube, (f) connection of said reagent tube and said tube along an axis which is not parallel, and (g) attachment of said permeable tube to the opposite end of said tube.

9. The chemical sensing device of claim 8 wherein said first means for attaching said first reagent tube to said first fiber optic tube and said second means for attaching said second reagent tube to said second fiber optic tube are composed of heat shrink fluorocarbon polymer.

10. The chemical sensing device of claim 8 wherein said first reagent tube and said second reagent tube are composed of fluorocarbon polymer.

11. The chemical sensing device of claim 8 wherein the permeable tube is formed into a loop.

12. The chemical sensing device of claim 8 wherein the permeable tube is formed without a loop.

13. The chemical sensing device of claim 8 wherein said first fiber optic tube and said second fiber optic tube are composed of fluorocarbon polymer.

14. The chemical sensing device of claim 8 wherein said first fiber optic tube and said second fiber optic tube are composed of heat shrink fluorocarbon polymer.

* * * * *